United States Patent [19]

Markus

[11] Patent Number: 4,589,631
[45] Date of Patent: May 20, 1986

[54] SURGICAL STAPLE REMOVER

[75] Inventor: Richard L. Markus, Bridgeport, Conn.

[73] Assignee: United States Surgical Corporation, Norwalk, Conn.

[21] Appl. No.: 655,636

[22] Filed: Sep. 28, 1984

[51] Int. Cl.$^4$ .......................................... B25C 11/00
[52] U.S. Cl. ...................................................... 254/28
[58] Field of Search ................... 254/28; 81/416, 418, 81/421, 422, 423

[56] References Cited

U.S. PATENT DOCUMENTS

| D. 271,742 | 12/1983 | Li et al. | D8/48 |
|---|---|---|---|
| 3,283,557 | 11/1966 | Wood | 72/386 |
| 3,344,649 | 10/1967 | Wood | 72/392 |
| 3,833,953 | 9/1974 | Fisher et al. | 81/416 |
| 3,926,195 | 12/1975 | Bleier et al. | 128/346 |
| 4,026,520 | 5/1977 | Rothfuss et al. | 254/28 |
| 4,073,179 | 2/1978 | Hickey et al. | 72/409 |
| 4,465,071 | 8/1984 | Samuels et al. | 128/335 |

FOREIGN PATENT DOCUMENTS

0059778A1 9/1982 European Pat. Off. .
0107157A1 5/1984 European Pat. Off. .
WO83/00428 2/1983 PCT Int'l Appl. .

Primary Examiner—Frederick R. Schmidt
Assistant Examiner—Judy J. Hartman
Attorney, Agent, or Firm—Robert R. Jackson; John E. Nathan

[57] ABSTRACT

A surgical staple remover has two pivotally connected arms, each of which is made up of a proximal handle piece and a distal nose piece. All four pieces are held together by a single pivot pin, and the handle and nose pieces of each arm interfit with one another so that both pieces of each arm pivot as a unit about the pivot pin. The nose piece of a first arm includes two, small, laterally spaced members which can be slipped under the backspan of a surgical staple to be removed. The nose piece of the second arm includes a single member which is initially between and above the two laterally spaced members. When the arms are manually squeezed together, the single member bends the center of the staple backspan down between the laterally spaced members and pivots the legs of the staple out of the tissue.

9 Claims, 11 Drawing Figures

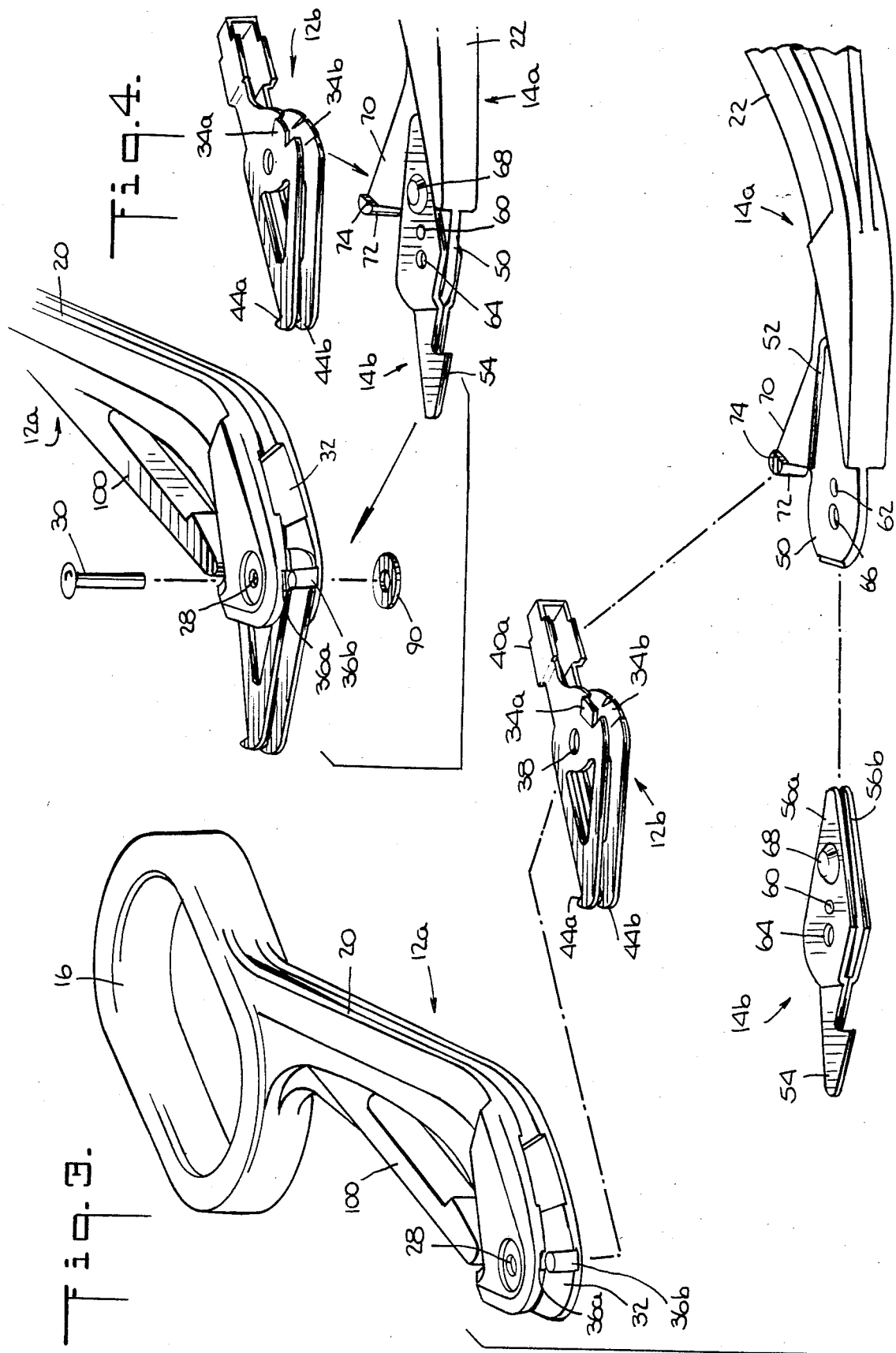

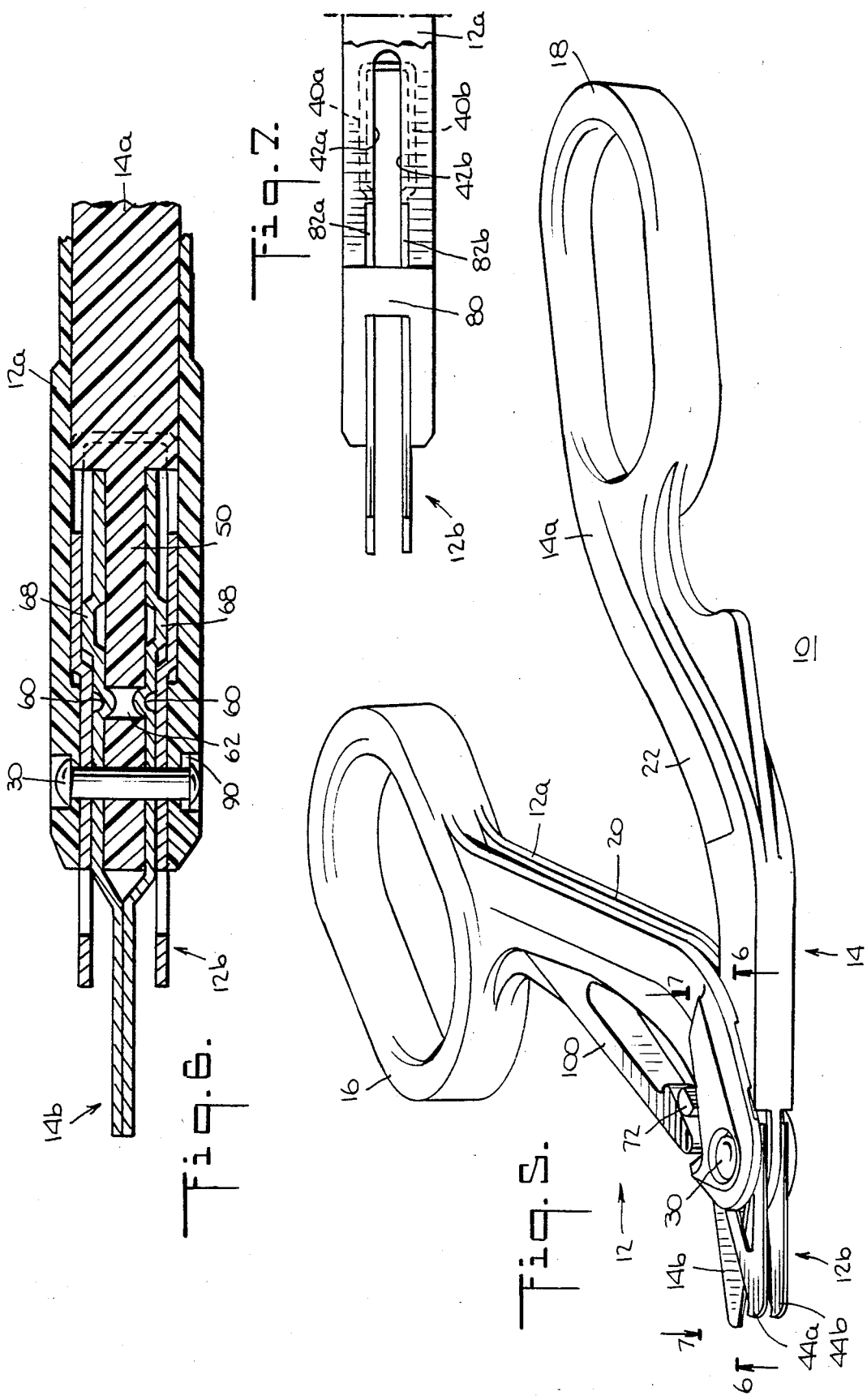

SURGICAL STAPLE REMOVER

BACKGROUND OF THE INVENTION

This invention relates to surgical stapling, and more particularly to apparatus for removing metal surgical staples from body tissue (e.g., skin tissue) to which the staples have been applied.

There is a need for a surgical staple remover which is both inexpensive and reliable. It is desirable to provide surgical staple removers which are relatively inexpensive so that the device can be discarded after use on a single patient, thereby avoiding all difficulty and expense associated with cleaning and sterilizing the apparatus for reuse. This is especially important in the case of skin staple removers because skin staples are frequently removed in a doctor's office or outpatient facility where instrument cleaning and sterilizing equipment is not available and where instrument cleaning and sterilizing would interfere with efficient operation of the facility.

Despite the requirement for low cost, it is important that the staple remover work reliably because it performs a surgical procedure, albeit a relatively minor one.

It is therefore an object of this invention to improve and simplify surgical staple removers.

It is another object of this invention to provide a reliable and efficient surgical staple remover having a minimal number of easily manufactured and assembled parts.

SUMMARY OF THE INVENTION

These and other objects of the invention are accomplished in accordance with the principles of the invention by providing a surgical staple remover which can be made up of only four parts held together by a single pivot pin. The surgical stapler has two pivotally connected arms, each of which is made up of a proximal handle piece and a distal nose piece. All for pieces are secured together by the single pivot pin, and the handle and nose pieces of each arm interfit with one another so that both pieces of each arm pivot as a unit about the pivot pin. A first of the handle pieces includes a finger which extends through a slot in the second handle piece. A spring finger integrally formed on the second handle piece presses on the end of the first handle piece finger to resiliently bias the arms of the staple remover apart. Shoulders on the first handle piece finger contact shoulders on the second handle piece to act as a stop for limiting the amount of separation of the arms. The nose piece of the second handle piece arm includes two, small, laterally spaced members which can be slipped under the backspan of a surgical staple to be removed. The nose piece of the first handle piece arm includes a single member which is initially between and above the two laterally spaced members on the other arm. When the arms of the staple remover are manually squeezed together, the single member bends the center of the staple backspan down between the laterally spaced members and pivots the legs of the staple out of the tissue.

Further features of the invention, its nature and various advantages will be more apparent from the accompanying drawings and the following detailed description of the invention.

BRIEF DESCRIPTION OF THE DRAWINGS

FIGS. 3 and 4 are exploded partial perspective views of the apparatus of FIGS. 1 and 2.

FIG. 5 is another perspective view of the apparatus of FIGS. 1-4.

FIG. 6 is a sectional view taken along the line 6—6 in FIG. 5.

FIG. 7 is a view of a portion of the apparatus taken along the line 7—7 in FIG. 5.

DETAILED DESCRIPTION OF THE INVENTION

Figure 1:
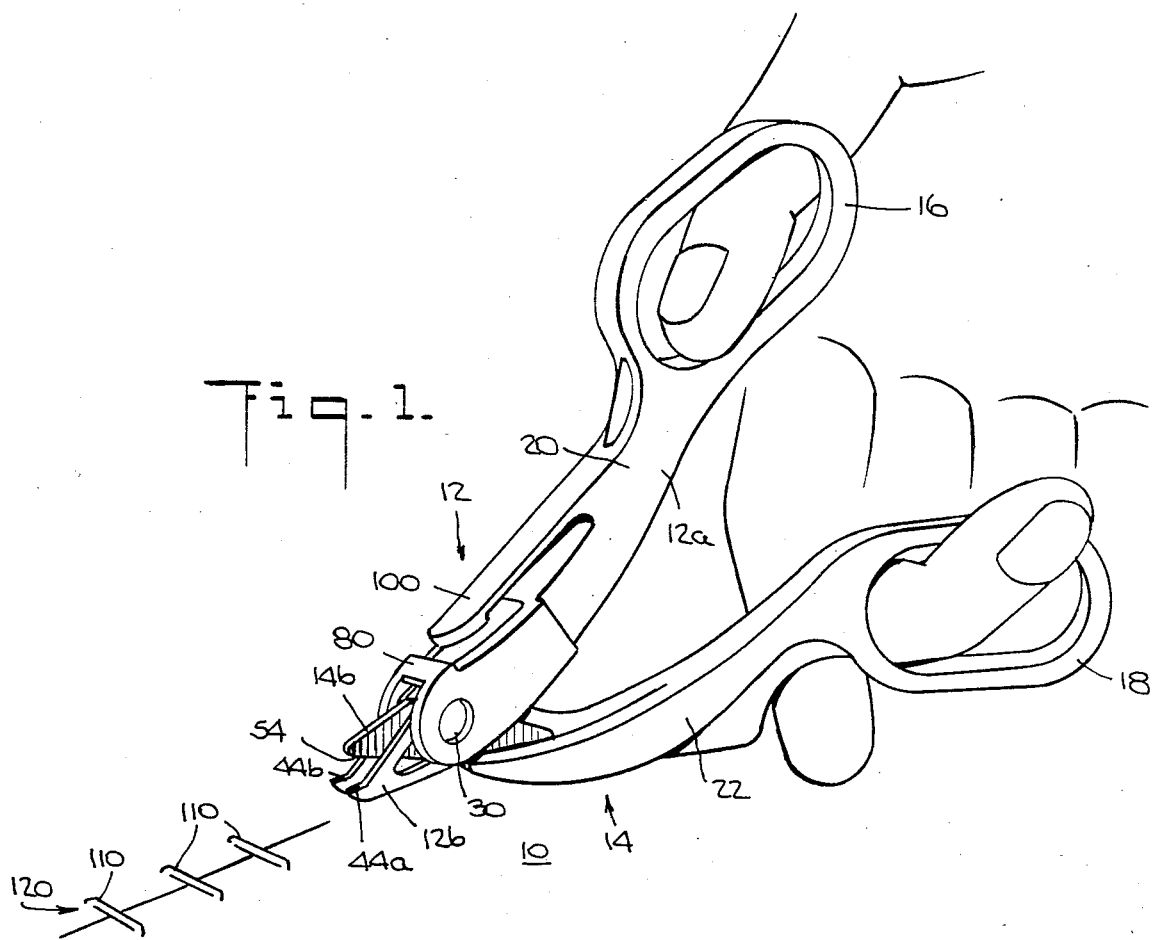
FIG. 1 is a perspective view of an illustration embodiment of the surgical staple remover of this invention.

The surgical staple remover 10 of this invention includes upper and lower, pivotally connected scissor-type arms 12 and 14, respectively. As is best seen in FIG. 3, each arm is made up of two pieces: a proximal handle piece 12a or 14a, and a distal nose piece 12b or 14b, respectively. Each handle piece has a proximal ring handle portion 16 or 18, an intermediate longitudinal shaft portion 20 or 22, and a distal portion which interfits with the associated nose piece. Arms 12 and 14 are pivotally connected to one another by pivot pin 30 which is located in the area in which each handle piece joins the associated nose piece.

Each of handle pieces 12a and 14a is preferably made of a plastic material, and each is preferably molded as one piece. Each of nose pieces 12b and 14b is preferably made of a single piece of sheet metal.

The distal end portion of handle piece 12a includes a longitudinal slot or bifurcation 32 (FIG. 3) within which nose piece 12b is inserted. Handle piece 12a is transversely reinforced across slot 32 by bridge 80 (FIG. 1). Nose piece 12b is secured within handle piece 12a by pin 30 extending through handle piece aperture 28 and nose piece aperture 38. Nose piece 12b is constrained to pivot with handle piece 12a by virtue of the presence of outwardly projecting nose piece ears 34a and 34b in handle piece slots 36a and 36b, respectively. Slots 36a and 36b extend radially downwardly from handle piece aperture 28. Additional pivoting force is applied to nose piece 12b from handle piece 12a by virtue of the fact that proximal upwardly facing nose piece surfaces 40a and 40b bear on inwardly projecting handle piece shoulders 42a and 42b, respectively, near the proximal end of slot 32 (see FIGS. 7-9). Nose piece 12b is generally U-shaped, with the base of the U being adjacent the proximal end of slot 32 and with each leg of the U lying along a respective one of the side surfaces of slot 32.

The distal end of handle piece 14a has a relatively thin, blade-like area 50. The proximal end portion of each surface of blade-like area 50 is bounded by a concave V-shaped shoulder 52. Nose piece 14b is sharply folded back on itself along distal line 54. The two proximally extending portions 56a and 56b of nose piece 14b are laterally spaced from one another so that blade 50 fits snugly between them. The proximal peripheral edges of nose piece portions 56a and 56b are convexly V-shaped and are received against and mate with shoulders 52. Inwardly directed dimples 60 (FIG. 6) in nose piece 14b extend into aperture 62 through blade-like area 50 and help hold nose piece 14b on handle piece 14a during assembly of the apparatus. In the assembled apparatus, nose piece 14b is secured to handle piece 14a by pivot pin 30 which extends through nose piece aperture 64 and handle piece aperture 66. Nose piece 14b is constrained to pivot with handle piece 14a by the interfitting relationship between nose piece surfaces 56 and handle piece surfaces 52.

Handle piece 14a includes upwardly extending finger 70. The upper end of finger 70 has a slightly enlarged head 72 with a downwardly facing shoulder 74 on each side of finger 70 where head 72 joins finger 70.

The assembly of the apparatus is shown in FIGS. 3 and 4. Nose piece 14b is slipped onto blade-like area 50 of handle piece 14a so that dimples 60 enter aperture 62 and apertures 64 and 66 are coaxial. Nose piece 12b is then slipped over finger 70 on handle 14a, and subassembly 12b, 14a, and 14b is inserted into slot 32 from below so that apertures 28 and 38 are coaxial and so that ears 34 enter slots 36. As this is done—and before apertures 28 and 38 are brought into alignment with apertures 64 and 66—the enlarged head 72 of finger 70 can pass through the laterally enlarged portion of nose portion 12b below surfaces 40a and 40b and out through the top of handle piece 12a via slots 82a and 82b (FIG. 7) between bridge 80 and shoulders 42. Thereafter, all of apertures 28, 38, 64, and 66 are aligned, pin 30 is inserted through the aligned apertures, washer 90 is put on the end of pin 30, and pin 30 is upset or clinched beyond washer 90 (see FIG. 6) to convert the pin into a double-headed rivet and thereby prevent disassembly of the apparatus. Outwardly extending pads 68 on each side of lower arm nose piece 14b fit snugly against the adjacent sides of slot 32 in upper arm handle piece 12a. This prevents upper and lower arms 12 and 14 from wobbling on pin 30. The extreme distal end 54 of lower nose piece 14b is above and between the laterally spaced extreme distal end portions 44a and 44b of upper nose piece 12b.

In the fully assembled apparatus, shoulders 74 on lower arm 14 are above shoulders 42 on upper arm 12. Contact between shoulders 74 and shoulders 42 prevents lower arm 14 from pivoting downwardly relative to upper arm 12 beyond the position shown in FIGS. 1 and 2 (see also FIG. 8). Shoulders 74 and 42 therefore cooperate to act as a return stroke stop for the apparatus.

Figure 2:
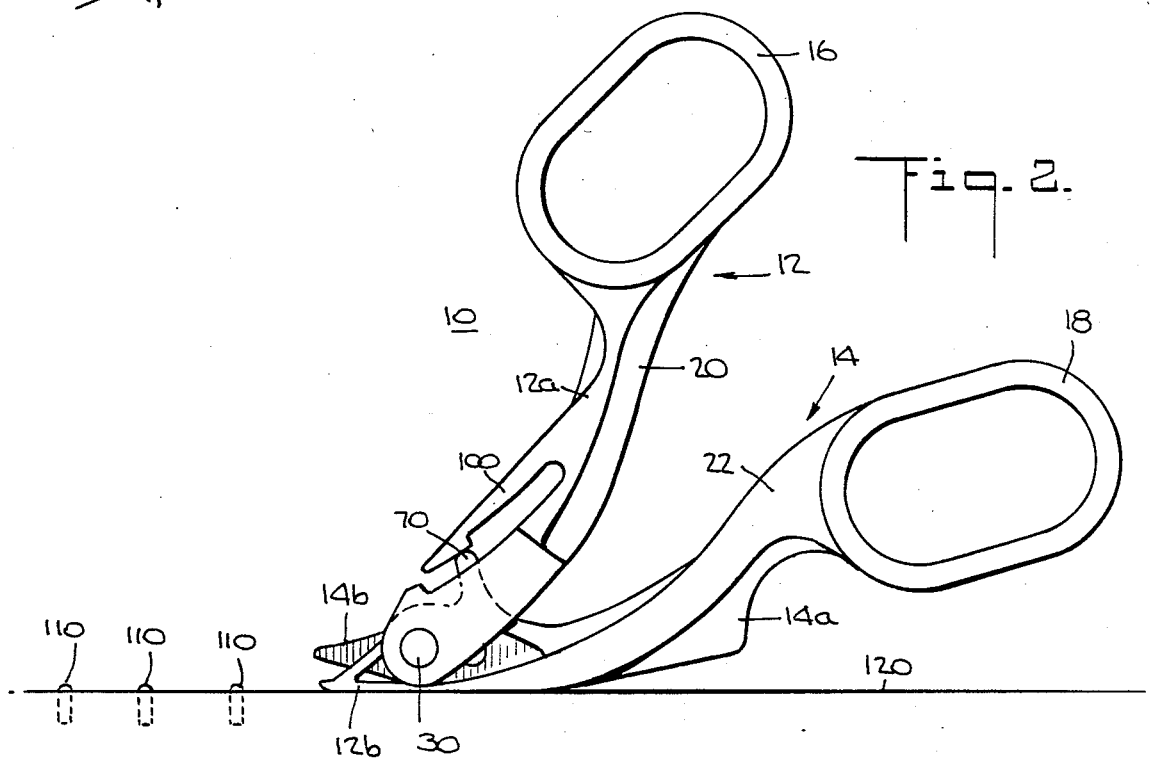
FIG. 2 is a aside elevational view of the apparatus of FIG. 1.
Figure 9:
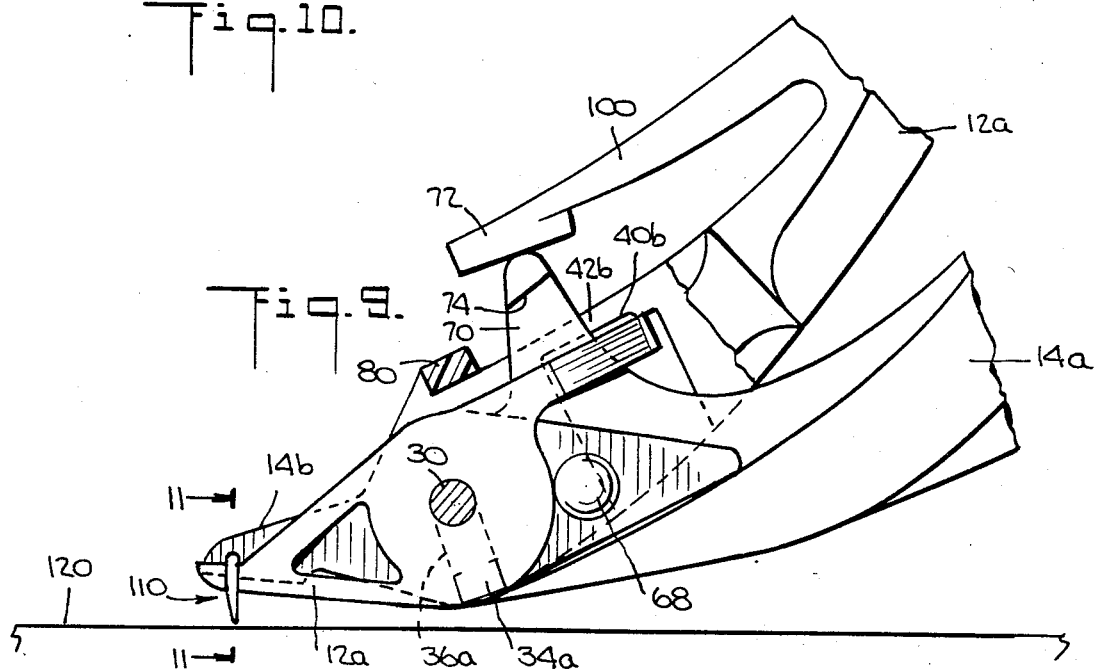
FIG. 9 is a view similar to FIG. 8 but showing a subsequent stage in the operation of the apparatus.

The assembled apparatus is resiliently biased toward the open position shown in FIGS. 1 and 2 by the pressure of the distal end of spring finger 100, which is formed integrally with upper handle piece 12a, on the upper end of lower arm finger 70. When the apparatus is operated by manually squeezing ring handles 16 and 18 together, finger 70 deflects spring finger 100 upwardly as shown in FIG. 9. When the manual pressure on handles 16 and 18 is relieved, the downward pressure of spring finger 100 on finger 70 automatically restores the apparatus to its initial condition. As mentioned above, the return stroke stops when shoulders 74 contact shoulders 42.

Figure 8:
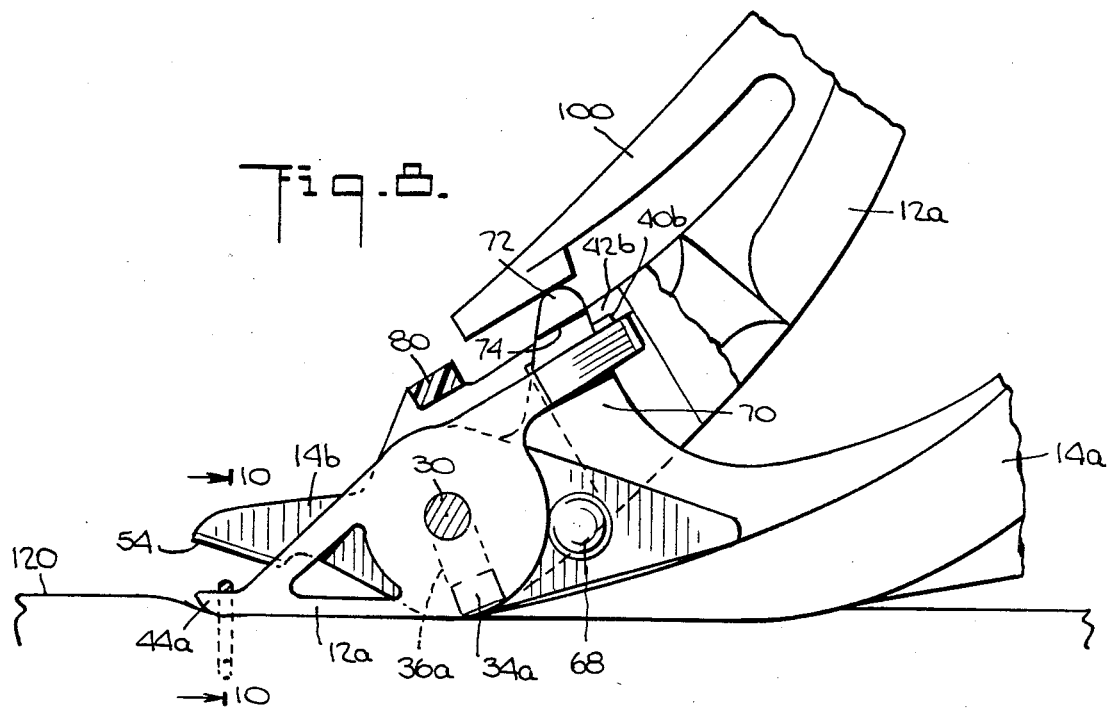
FIG. 8 is a partly sectional elevational view of the distal portion of the apparatus of FIGS. 1-7 showing one stage in the operation of that apparatus.
Figures 10, 11:
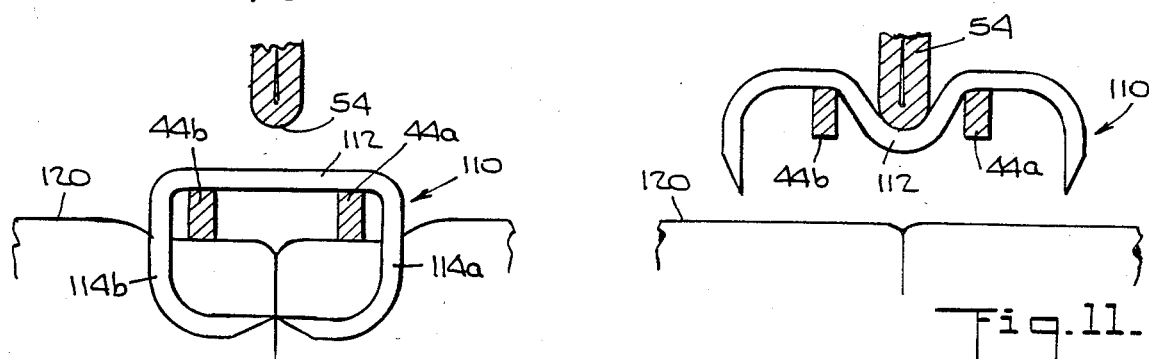
FIGS. 10 and 11 are sectional views respectively taken along the lines 10—10 and 11—11 in FIGS. 8 and 9.

Use and operation of the staple remover are further illustrated in FIGS. 8–11. With ring handles 16 and 18 apart as shown in FIGS. 1 and 2, the extreme distal end portions 44 of upper nose piece 12b are slipped under the backspan 112 of surgical staple 110 which is in place in body tissue (typically skin tissue) 120 as shown in FIGS. 8 and 10. The lateral spacing of distal end portions 44 is less than the lateral spacing of staple legs 114a and 114b. The lower ends of legs 114 are typically turned in toward one another to secure and staple in the tissue.

When the distal end portions 44 are in position under backspan 112, ring handles 16 and 18 are manually squeezed together. This causes lower arm distal end portion 54 to move down against backspan 112 between upper arm distal end portions 44. Distal end portion 54 bends the center of backspan 112 down between end portions 44 as best seen in FIG. 11. This causes staple legs 114 to effectively pivot out of tissue 120 with minimal damage to the tissue (see also FIG. 9). The extracted staple can be carried away from the tissue by the staple remover and then released from the staple remover and discarded by releasing the manual pressure on ring handles 16 and 18. The staple remover is now ready to remove another staple.

I claim:

1. A surgical staple remover comprising:

a first longitudinal handle piece having a proximal handle portion and a distal aperture transverse to a first longitudinal axis which extends from the handle portion to the aperture of the first handle piece;

a second longitudinal handle piece having a proximal handle portion and a distal aperture transverse to a second longitudinal axis which extends from the handle portion to the aperture of the second handle piece, the first and second longitudinal axes intersecting at the apertures of the first and second handle pieces and thereby defining a first plane to which the apertures of the first and second handle pieces are perpendicular;

a first longitudinal nose piece having (a) a distal nose portion including two laterally spaced, distally extending fingers parallel to the first plane, (b) an intermediate aperture perpendicular to the first plane, and (c) proximal surfaces transverse to the first plane and nonconcentric with the aperture of the first nose piece, the proximal surfaces of the first nose piece mating with distal surfaces of the first handle piece when the aperture in the first handle piece and the aperture in the first nose piece are coaxial so that the first handle piece and the first nose piece pivot as a unit about the coaxial apertures;

a second longitudinal nose piece having (a) a distal nose portion including a single distally extending finger laterally intermediate the two laterally spaced fingers and parallel to the first plane, (b) an intermediate aperture perpendicular to the first plane, and (c) proximal surfaces transverse to the first plane and nonconcentric with the aperture of the second nose piece, the proximal surfaces of the second nose piece mating with distal surfaces of the second handle piece when the aperture in the second handle piece and the aperture in the second nose piece are coaxial so that the second handle piece and the second nose piece pivot as a unit about the coaxial apertures; and a pivot pin through the coaxial apertures in all of the first and second pieces, the pivot pin being the sole means for holding together any two of the first and second handle pieces and the first and second nose pieces.

2. The apparatus defined in claim 1 wherein the pivot pin is a double headed rivet.

3. The apparatus defined in claim 1 wherein the first and second handled pieces are made of plastic and the first and second nose pieces are made of metal.

4. The apparatus defined in claim 3 wherein each of the first and second handle pieces and each of the first and second nose pieces is unitary.

5. The apparatus defined in claim 1 wherein the second handle piece includes an intermediate first finger extending transversely in the direction away from the longitudinal axis of the second handle piece and toward the longitudinal axis of the first handle piece, the first finger having a first shoulder surface facing toward the longitudinal axis of the second handle piece, and wherein the first handle piece includes (a) a second resilient spring finger for contacting the first finger and for resiliently urging the first finger in the direction of the longitudinal axis of the second handle piece, and (b) an intermediate second shoulder surface facing away from the longitudinal axis of the second handle piece for contacting the first shoulder surface to prevent the spring finger from pushing the first finger more than a predetermined distance in the direction of the longitudinal axis of the second handle piece.

6. The apparatus defined in claim 1 wherein the portion of each of the first handle piece and first nose piece adjacent the pivot pin is laterally bifurcated, and wherein the portion of each of the second handle piece and second nose piece adjacent the pivot pin passes through the bifurcation in the first handle piece and first nose piece.

7. A surgical staple remover comprising:
a first longitudinal handle piece having a proximal handle portion and a distal aperture transverse to a first longitudinal axis which extends from the handle portion to the aperture of the first handle piece;
a second longitudinal handle piece having a proximal handle portion and a distal aperture transverse to a second longitudinal axis which extends from the handle portion to the aperture of the second handle piece, the first and second longitudinal axes intersecting at the apertures of the first and second handle pieces and thereby defining a first plane to which the apertures of the first and second handle pieces are perpendicular;
a first longitudinal nose piece having (a) a distal nose portion includling two laterally spaced, distally extending fingers parallel to the first plane, (b) an intermediate aperture perpendicular to the first plane, and (c) proximal surfaces transverse to the first plane and nonconcentric with the aperture of the first nose piece, the proximal surfaces of the first nose piece mating with distal surfaces of the first handle piece when the aperture in the first handle piece and the aperture in the first nose piece are coaxial so that the first handle piece and the first nose piece pivot as a unit about the coaxial apertures;
a second longitudinal nose piece having (a) a distal nose portion including a single distally extending finger laterally intermediate the two laterally spaced fingers and parallel to the first plane, (b) an intermediate aperture perpendicular to the first plane, and (c) proximal surfaces transverse to the first plane and nonconcentric with the aperture of the second nose piece, the proximal surfaces of the second nose piece mating with distal surfaces of the second handle piece when the aperture in the second handle piece and the aperture in the second nose piece are coaxial so that the second handle piece and the second nose piece pivot as a unit about the coaxial apertures; and
a pivot pin through the coaxial apertures in the first and second handle pieces and the first and second nose pieces;
wherein the portion of each of the first handle piece and the first nose piece adjacent the pivot pin is laterally bifurcated, wherein the portion of each of the second handle piece and the second nose piece adjacent the pivot pin passes through the bifurcation in the first handle piece and first nose piece, wherein the second nose piece is also laterally bifurcated adjacent the pivot pin, and wherein the distal portion of the second handle piece extends into the bifurcation in the second nose piece.

8. The apparatus defined in claim 7 wherein the bifurcated portion of the second nose piece has at least one inwardly extending dimple for releasably engaging an aperture in the portion of the second handle piece which extends into the bifurcation in the second nose piece.

9. The apparatus defined in claim 7 wherein the first nose piece is adjacent and bears on both inner surfaces of the bifurcation in the first handle piece, wherein the second nose piece is adjacent and bears on both inner surfaces of the bifurcation in the first nose piece, and wherein the second nose piece includes proximal, outwardly extending pads for contacting both inner surfaces of the bifurcation in the first handle piece at a location which is spaced from the pivot pin.

* * * * *